United States Patent
Jennissen et al.

(10) Patent No.: US 10,376,613 B2
(45) Date of Patent: Aug. 13, 2019

(54) PROCESS FOR THE PRODUCTION OF STORABLE IMPLANTS WITH AN ULTRAHYDROPHILIC SURFACE

(71) Applicant: Herbert Jennissen, Cologne (DE)

(72) Inventors: Herbert Jennissen, Cologne (DE); Steffen Lüers, Essen (DE); Markus Laub, Essen (DE)

(73) Assignee: Nobel Biocare Services AG, Kloten (CH)

( * ) Notice: Subject to any disclaimer, the term of this patent is extended or adjusted under 35 U.S.C. 154(b) by 279 days.

(21) Appl. No.: 14/949,994

(22) Filed: Nov. 24, 2015

(65) Prior Publication Data

US 2016/0136336 A1    May 19, 2016

Related U.S. Application Data (63) Continuation of application No. 12/527,175, filed as application No. PCT/EP2008/051764 on Feb. 13, 2008, now Pat. No. 9,242,029.

(30) Foreign Application Priority Data

Feb. 14, 2007    (DE) .................. 10 2007 007 865

(51) Int. Cl.
    *A61L 31/08*    (2006.01)
    *B05D 1/18*    (2006.01)
    (Continued)

(52) U.S. Cl.
    CPC .......... *A61L 31/088* (2013.01); *A61F 2/0095* (2013.01); *A61L 27/22* (2013.01);
    (Continued)

(58) Field of Classification Search
    CPC .................................................. A61M 25/00
    (Continued)

(56) References Cited

U.S. PATENT DOCUMENTS

| | | | |
|---|---|---|---|
| 4,013,576 | A | 3/1977 | Loshaek |
| 4,504,405 | A | 3/1985 | Howes |

(Continued)

FOREIGN PATENT DOCUMENTS

| | | |
|---|---|---|
| EP | 0 987 031 A1 | 3/2000 |
| EP | 1 847 278 A1 | 4/2006 |

(Continued)

OTHER PUBLICATIONS

Chatzinikolaidou et al., Biocoating of Electropolished and Ultra-Hydrophilic Titanium and Cobalt Chromium Molybdenum Alloy Surfaces with Proteins, 2002, Mat.-wiss u, Werkstofftech, vol. 33, pp. 720-727 (Year: 2002).*

(Continued)

*Primary Examiner* — Dah-Wei D. Yuan
*Assistant Examiner* — Andrew J Bowman
(74) *Attorney, Agent, or Firm* — Cahn & Samuels, LLP (57) ABSTRACT

The present invention concerns a process for the production of implants with an ultrahydrophilic surface as well as the implants produced in that way and also processes for the production of loaded, so-called bioactive implant surfaces of metallic or ceramic materials, which are used for implants such as artificial bones, joints, dental implants or also very small implants, for example what are referred to as stents, as well as implants which are further produced in accordance with the processes and which as so-called "delivery devices" allow controlled liberation, for example by way of dissociation, of the bioactive molecules from the implant materials.

7 Claims, 5 Drawing Sheets

(51) Int. Cl.
*A61L 27/22* (2006.01)
*A61L 27/50* (2006.01)
*A61F 2/00* (2006.01)
*A61L 31/02* (2006.01)
*A61L 31/04* (2006.01)
*A61L 31/16* (2006.01)
*B65D 81/22* (2006.01)

(52) U.S. Cl.
CPC .............. *A61L 27/50* (2013.01); *A61L 31/022* (2013.01); *A61L 31/047* (2013.01); *A61L 31/16* (2013.01); *B05D 1/18* (2013.01); *B65D 81/22* (2013.01); *A61L 2300/102* (2013.01); *A61L 2300/252* (2013.01); *A61L 2300/608* (2013.01); *A61L 2400/18* (2013.01); *A61L 2420/08* (2013.01)

(58) Field of Classification Search
USPC ........................................................ 604/265
See application file for complete search history.

(56) References Cited

U.S. PATENT DOCUMENTS

| | | | |
|---|---|---|---|
| 4,664,666 A * | 5/1987 | Barrett | A61F 2/16 623/6.44 |
| 5,141,507 A | 8/1992 | Parekh | |
| 6,635,269 B1 | 10/2003 | Jennisen | |
| 6,702,855 B1 | 3/2004 | Steinmann et al. | |
| 6,911,472 B2 | 6/2005 | Hedge et al. | |
| 7,579,005 B2 | 8/2009 | Keeler et al. | |
| 7,740,481 B2 | 6/2010 | Cigada et al. | |
| 2004/0049287 A1 | 3/2004 | Descouts et al. | |
| 2004/0074568 A1 | 4/2004 | Jennissen | |
| 2004/0109937 A1 | 6/2004 | Jennissen et al. | |
| 2004/0167085 A1 | 8/2004 | Hedge et al. | |
| 2004/0210309 A1 | 10/2004 | Denzer et al. | |
| 2005/0079201 A1 | 4/2005 | Rathenow et al. | |
| 2005/0143817 A1 | 6/2005 | Hunter et al. | |
| 2005/0149080 A1 | 7/2005 | Hunter et al. | |
| 2006/0147492 A1 | 7/2006 | Hunter et al. | |
| 2006/0217777 A1 | 9/2006 | Strom et al. | |
| 2007/0005024 A1* | 1/2007 | Weber | A61L 29/14 604/265 |
| 2007/0299535 A1 | 12/2007 | Ihde | |
| 2009/0132048 A1* | 5/2009 | Denzer | A61C 8/0012 623/16.11 |
| 2009/0164027 A1 | 6/2009 | Zipprich | |

FOREIGN PATENT DOCUMENTS

| | | |
|---|---|---|
| EP | 1 872 805 A2 | 6/2007 |
| WO | 1999/26674 A | 6/1999 |
| WO | 00/44305 | 8/2000 |
| WO | 0044305 A1 | 8/2000 |
| WO | 0209788 A1 | 2/2002 |
| WO | 03/030957 A1 | 4/2003 |
| WO | 2005046516 A2 | 5/2005 |
| WO | 2007118734 A1 | 10/2007 |
| WO | 2009/097218 A1 | 8/2009 |

OTHER PUBLICATIONS

E1, Saline (medicine), 2018, Wikipedia, https://en.wikipedia.org/wiki/Saline_(medicine) (Year: 2018).*
Rupp, F., et al., "Enhancing Surface Free Energy and Hydrophilicity Through Chemical Modification of Microstructured Titanium Implant Surfaces," J. Biomed. Mater. Res., 323-334, 2005.
Camlog Biotechnologies, Press Release "Osteoinduktion ist der Motor des Fortschritts in der oralen Implantologie," Dec. 2006.
Wikipedia.com, "Isotonische Kochsalzlösung,", printed Dec. 29, 2011.
English Abstract of WO 00/44305.
English Abstract of WO 03/030957.
English Abstract of EP 1 872 805.
English Abstract of EP 1 847 278.
Wikipedia.com, "Saline (medicine)", printed Aug. 1, 2013.
Filing of a New Opposition in EP 2 121 058 B1 dated Apr. 1, 2012.
International Preliminary Report on Patentability and Written Opinion, dated Sep. 8, 2009.
English Abstract of WO0209788, Feb. 7, 2002.
English Abstract of EP1150620 dated Nov. 7, 2001 (corresponding to WO 0044305).
M. Chatzinikolaidou et al: "Stability of Surface-Enhanced Ultrahydrophilic Metals as a Basis for Bioactive rhBMP-2 Surfaces," Materialwissenschaft Und Werkkstofftechnik, VCH Verlagsgesellschaft. Weinheim, DE, vol. 34, No. 12, 2003, pp. 1106-1112.
Jennissen H.P. et al: "Biocoating of Implants with Mediator Molecules: Surface Enhancement of Metals by Treatment with Chromosulfuric Acid/Biologisierung von Implantaten Mit Biomolekuelen: Oberflaechenverdelung Von Metallen Durch Behandliung Mit Chromoschwefelsaeure." Materialwissenschaft Und Werkstofftechnik. VCH Verlagsgeellschaft, Weinheim, DE, vol. 30, No. 2, Jan. 1, 1999, pp. 838-845.
Jennissen Herbert, P.: "Ultra-Hydrophilic Transition Metals as Histophiliv Biomaterials." Macromolecular Symposia, Wiley VH Verlag. Weinheim, DE, vol. 225, May 1, 2005, pp. 43-69.
Dan Patel. Re: Why does plain water evaporate faster than saltwater. 1999. http://www.madsci.org/posts/archives/1999-12/944144707.Ch.r.html.
M. Chatzinikolaidou et al., "Biocoating of Electropolished and Ultra-Hydrophilic Titanium and Cobalt Chromium Molybdenum Alloy Surfaces with Proteins", Mat.-wiss u. Werkstofftech. 33, 720-727 (2002).
Abstract of WO2005046516A2, May 26, 2005.

* cited by examiner

PROCESS FOR THE PRODUCTION OF STORABLE IMPLANTS WITH AN ULTRAHYDROPHILIC SURFACE

This application is a Continuation Application of U.S. Ser. No. 12/527,175 filed in the U.S. Patent and Trademark Office on 19 Feb. 2010, which is a U.S. national stage application of PCT international application PCT/EP2008/051764 filed on 13 Feb. 2008, and claims priority to German patent document 10 2007 007 865.1 filed on 14 Feb. 2007, the entireties of which are incorporated herein by reference.

BACKGROUND OF INVENTION

The present invention concerns a process for the production of implants with an ultrahydrophilic surface as well as the implants produced in that way and also processes for the production of loaded, so-called bioactive implant surfaces of metallic or ceramic materials, which are used for implants such as artificial bones, joints, dental implants or also very small implants, for example what are referred to as stents, as well as implants which are further produced in accordance with the processes and which as so-called "delivery devices" allow controlled liberation, for example by way of dissociation, of the bioactive molecules from the implant materials.

The implantation of artificial joints or bones has become of increasing significance in recent years, for example in the treatment of joint dysplasias or luxations or in the case of diseases which can result from the wear of joints as a consequence of joint misplacements. The function of the implants and the materials which are used for the manufacture thereof and which, besides metals such as titanium or metal alloys, can also include ceramic or plastic materials such as Teflon or polylactides, are being continuously improved so that after a successful healing progress in 90-95% of cases implants can have lives of 10 years.

Irrespective of those advances and improved operative methods, implantation is still a difficult and burdensome intervention, in particular as it is linked to a tedious healing process for the implant, which often includes clinic and cure treatment stays of months in length, including rehabilitation measures. Besides the pains in that respect the length of the treatment period and the fact of being taken out of familiar surroundings represent major stresses for the patients concerned. In addition the tedious healing process gives rise to high levels of personnel and nursing costs due to the intensive care required.

Knowledge of the processes at the molecular level, which are required for an implant to successfully grow in place, has become significantly enlarged in recent years. Structure compatibility and surface compatibility are crucial for tissue compatibility of an implant. Biocompatibility in the narrower sense is governed solely by the surface. Proteins play a crucial part at all levels in integration. As explained hereinafter they already decide during the implantation operation, due to the formation of an initial adsorbed protein layer, about the further progress in terms of implant healing as the first cells are later established on that layer.

In the molecular interaction between implant which is also referred to as biomaterial and tissue, a large number of reactions occur, which seem to be arranged in a strictly hierarchical fashion. The adsorption of proteins at the surface of the biomaterial takes place as the first biological reaction. Then, in the protein layer which is produced as a result, individual protein molecules are transformed for example by conformation changes to signalling substances which are presented on the surface, or protein fragments acting as signalling substances are liberated by catalytic (proteolytic) reactions.

Triggered by the signalling substances, in the next phase cellular colonisation takes place, which can include a large number of cells such as leucocytes, macrophages, immunocytes and finally also tissue cells (fibroblasts, fibrocytes, osteoblasts, osteocytes). In that phase other signalling substances, so-called mediators such as for example cytokines, chemokines, morphogens, tissue hormones and genuine hormones play a crucial part. In the case of biocompatibility the situation finally involves integration of the implant in the overall organism and ideally a permanent implant is achieved.

In the light of works which have been carried out in recent years at the molecular level of osteogenesis, chemical signalling substances, the so-called "bone morphogenic proteins" (BMP-1-BMP-15) which influence bone growth have become of increasing significance. BMPs (in particular BMP-2 and BMP-4, BMP-5, BMP-6, BMP-7) are osteoinductive proteins which stimulate bone regeneration and bone healing insofar as they cause proliferation and differentiation of precursor cells to give osteoblasts. In addition they promote the formation of alkaline phosphatases, hormone receptors, bone-specific substances such as collagen type 1, osteocalcin, osteopontin and finally mineralisation.

In that respect the BMP molecules regulate the three key reactions of chemotaxis, mitosis and differentiation of the respective precursor cell. In addition BMPs play an important part in embryogenesis, organogenesis of the bone and other tissue, in which respect osteoblasts, chondroblasts, myoblasts and vascular smooth muscle cells (proliferation inhibition by BMP-2) are known as target cells.

In the meantime 15 BMPs inclusive of multiple isoforms are known. Except for the BMP-1 the BMPs belong to the "transforming growth factor beta" (TGF-β) superfamily, for which specific receptors are detected on the surfaces of the corresponding cells. As the successful use of recombinant human BMP-2 and/or BMP-7 has shown in experiments concerning defect healing processes on rats, dogs, rabbits and monkeys, there does not appear to be any species specificity.

Previous attempts to utilise the bone growth-triggering properties of the BMPs specifically for implantation purposes, by the BMP-2 and/or BMP-7 being applied directly to metallic or ceramic biomaterials have however been substantially unsuccessful.

A series of works in the field of coated implant materials is known in the state of the art. Thus WO9926674 describes a process for the production of bioactive implant surfaces of metallic or ceramic materials, in which in a first step anchor molecules are covalently bonded to the surface of the implant material and in a second step peptides are covalently bonded to the anchor molecules.

WO0209788 provides a process for the production of bioactive implant surfaces of metallic or ceramic materials, in which in a first step anchor molecules with hydrophobic residues are covalently bonded to the surface of the implant material and in a second step peptides are applied to the implant material treated in that way, which are immobilised as a consequence of non-covalent interactions between the peptides and the hydrophobic residues of the anchor molecules.

In accordance with those two documents it is therefore necessary to chemically immobilise on the surface of the implant anchor molecules which are then covalently chemically bonded to the peptides or which are bonded on the implant surface as a result of non-covalent interactions. Test results by the inventors have shown in that respect that attempts to immobilise peptides on the implant surface without anchor molecules were not successful.

It was now found by the inventors surprisingly, in particular in regard to those earlier attempts on the part of the inventors to implement immobilisation, that immobilisation of peptides on metal surfaces, in particular growth factors of the TGF class, for example BMP proteins, can be achieved if a sufficiently hydrophilic surface can be provided on the implant material. It was found by the inventors that this can be achieved if an ultrahydrophilic oxide layer is produced on the metal surface by treatment with an oxidation agent.

In that respect the invention makes use of the fact that surfaces with a high surface energy can have strong tissue bioadhesion. As surfaces with a high surface energy generally have low contact angles with water, such a surface can be very easily identified by way of the measurement of dynamic contact angles. Small contact angles characterise a high level of wettability of a surface.

In respect of the dynamic contact angles a distinction is drawn between an advancing angle ($\theta_A$) and a receding angle ($\theta_R$) and the difference in those angles is referred to as contact angle hysteresis. In that respect the advancing angle is characteristic of the hydrophilicity-hydrophobicity properties of a surface and substantially corresponds to what is referred to as the static contact angle. The greater the degree of hysteresis, the correspondingly greater is generally the heterogeneity of the surface. Mechanically polished or electro-polished titanium surfaces normally have dynamic contact angles (advancing angle) of 70-80° and in accordance with pertinent literature have a low tissue bioadhesion. Therefore in accordance with the inventors' development it is desirable to also provide surfaces with low contact angles on metals.

According to the invention surfaces with dynamic contact angles of between 0 and 10° are defined as "ultrahydrophilic". They have at the same time a characteristic nanostructure. In works involving animal experiments it was possible to show on the part of the inventors that bone density is twice as high after 4 weeks in the environment of an ultrahydrophilic implant, as in the environment of the control implant.

Admittedly the state of the art in accordance with EP 1 150 620 already described implants with hydrophilic surfaces after sand blasting and acid etching, on which wetting angles with water of between 20-50° were measured. Such surfaces are referred to as "hydrophilic" and could be preserved in given saline solutions. It will be noted however that it was observed in accordance with EP 1 150 620 that such surfaces were sensitive in relation to a rising salt concentration.

It has further been known in the state of the art for many years that hydrophilic metal surfaces, for example of titanium, are not stable but spontaneously become hydrophobic again. The chemical state of the surface of titanium and titanium-based alloys is complex. It is assumed that the surface of titanium metal oxidises spontaneously in air and water and that a reaction then occurs with water at the surface, that is to say in the outermost atom layer of the oxide, with hydroxyl groups being formed.

Accordingly such surfaces are particularly sensitive in relation to gamma sterilisation, a method which nowadays is widely used in the production of implants which can be clinically employed. Thus it was shown in the state of the art that titanium dioxide layers can be rendered hydrophilic by light irradiation. Those layers also lose their hydrophilicity after just a short time and become hydrophobic again, in which respect the precise mechanism in that change is still obscure.

Accordingly there is a need for a process which permits the production of implants which have unlimitedly stabilised ultrahydrophilic layers thereon and which at the same time withstand sterilisation.

SUMMARY OF INVENTION

The invention is therefore directed to a process for the production of an implant with an ultrahydrophilic surface, in which the surface of the implant is treated with an oxidation agent to achieve an oxide layer on the surface of the metal until a contact angle hysteresis of less than 10°, preferably less than 5°, when wetting the surface of the implant with water, is afforded, wherein the implant comprises a material which is selected from the group of metals, metallic alloys and combinations thereof with ceramic materials.

In that case the metal implant preferably comprises a material selected from the group of metals, metallic alloys and combinations thereof with ceramic materials. Preferably the implant material used comprises metallic materials such as pure titanium or metallic titanium alloys, chromium/nickel/aluminium/vanadium/cobalt alloys (for example TiAlV4, TiAlFe2,5), high-quality steels (for example V2A, V4A, chromium-nickel 316 L) or a combination thereof with ceramic materials such as hydroxyapatite, aluminium oxide, in which the metallic material is in the form of a composite material with ceramic material.

Accordingly ultrahydrophilic metal surfaces can be produced by means of the process according to the invention. For that purpose the surface of the metal implant is treated with an oxidation agent to achieve an oxide layer on the surface of the metal, until a contact angle hysteresis of less than 10°, preferably less than 5°, more preferably less than 1°, particularly preferably less than 0.5°, is afforded, when wetting with pure (distilled) water.

Preferably that treatment continues until the contact angle hysteresis is in the region of the minimum in the diagram when plotting the contact angle hysteresis against the time duration of the oxidation treatment.

That can be achieved in that the surface of the metal implant is treated with an oxidation agent, by the preferably degreased metal implant being shock-heated in hot chromosulphuric acid—preferably in that respect the chromosulphuric acid is of a density of more than 1.40 g/cm³—at a temperature of above 200° C., that is to say heated by immersion within a few seconds to the temperature of the chromosulphuric acid, and left there at that temperature for a period of 10 up to 90 minutes, preferably up to 60 minutes, particularly up to 30 minutes, and thereafter directly after removal the metal implant is cooled within a period of less than a minute, preferably within a few seconds, to room temperature. That can preferably be effected by the metal implant being quenched by immersion in concentrated sulphuric acid at a temperature of 15° C. to 25° C. To remove residues of acid and if present metal ions which are foreign to the implant, for example chromium ions, the surface of the metal implant is washed with distilled water in a plurality of washing steps (up to 15). If thereafter chromium ions are still to be found on the surface of the metal implant the metal implant can be treated with a solution of a chelating agent until it is no longer possible to detect metal ions. It was surprisingly found by the inventors that, when using EDTA as the chelating agent, the solution is coloured brown-violet to violet when chromium is dissolved out of the samples.

The inventors propose correspondingly for the situation that the samples are washed in 10% EDTA (1-3×) at pH 7, if required also in boiling EDTA solution, until coloration by chromium ions no longer occurs.

Thus, this process according to the invention makes it possible to produce an implant with an ultrahydrophilic surface which, in accordance with a further configuration of a process according to the invention, can be rendered storable.

For that purpose the inventors performed experiments which gave surprising results in comparison with the teachings known in the state of the art. By virtue of the cost aspect of wet packagings for preserving hydrophilic surfaces on implants which with the ultrahydrophilic metal implants according to the invention surprisingly permit storage-stable implants without wettability loss in relation to higher levels of salt concentration of more than 0.5 M/l, the search was also made for fluid-free packaging methods. In that respect it was surprisingly found that ultrahydrophilic titanium surfaces on which salt solutions were caused to evaporate became stable in relation to the wettability loss. Those salt solutions include for example 1M neutral salt solutions such as 1M NaCl, or also 5 mM EDTA pH 7.0. A particularly well-suited solution was found to be the buffer mixture with the following constituents:

120 to 150 mM NaCl
7.5 to 8.5 mM $Na_2HPO_4$
2.5 to 3.5 mM KCl
1.0 to 2.0 mM $KH_2PO_4$ at a pH-value of 7.2 to 7.6.

Evaporation can be effected under a protective gas or in atmospheric air, wherein the latter was used as standard because of its simplicity.

After evaporation a fine macroscopically invisible exsiccation layer was formed on the metal surface treated in that way, which in accordance with the invention stabilises and protects the ultrahydrophilicity. In general terms in accordance with the invention neutral salt solutions can be used in solution of an individual salt or also various salts in a concentration and amount which is inert in relation to the ultrahydrophilic surface and is sufficient after evaporation to cover the surface of the implant with the exsiccation layer. Evaporation can be performed when the implant is in the solution of neutral salt or when the implant has been removed from the solution and is thus only covered with a thin layer of that solution.

It was even more surprising that the stabilising action of the exsiccation layer is not nullified by gamma irradiation or other ionising radiation.

Figure 4A:
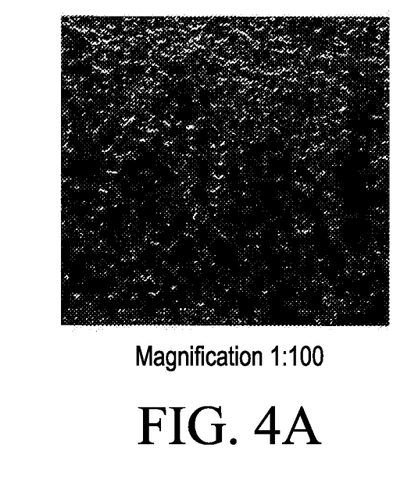
FIGS. 4A-4C show scanning electron-microscope recordings of chromosulphuric acid-treated SLA titanium plates (14×14×1.5 mm) after gamma sterilisation in an exsiccation buffer (60 min CSS with $HNO_3$, with quenching, gamma sterilised in PBS, $\theta=0°$) at magnification of 1:100 (FIG. 4A), a magnification of 1:10,000 (FIG. 4B), and a magnification of 1:100,000 (FIG. 4C).
Figure 4B:
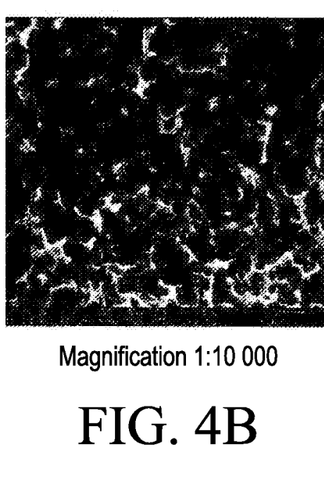
Figure 4C:
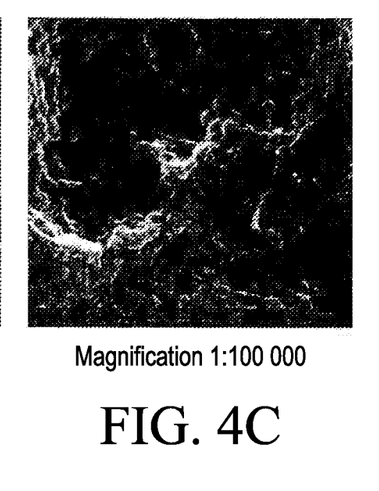

The inventors detected in a simple manner by means of scanning electron microscopy and EDX analysis whether such an exsiccation layer was formed according to the invention on a metal surface (see FIG. 4). It was further found that in general such an exsiccation layer is produced only when there are non-volatile constituents in the solution used. Such a layer does not occur for example when methanol, ethanol or acetone solutions are evaporated in the presence of ultrahydrophilic surfaces. The precise mechanism of stabilisation of the ultrahydrophilic layer by the exsiccation layer is still not clear, but could be related to electrostatic interactions between the electrolytes in the buffer solution and the charged groups on the metal surface. As only a very thin fluid layer of 0.1-0.2 µl/mm² is present on the metal surface for the exsiccation process upon removal from the buffer solution, for evaporation, the proportion of non-volatile substances in the exsiccation layer is only very slight and does not have to be removed from the implant for the implantation operation. As already mentioned the "ultrahydrophilic" surface differs from the "hydrophilic" surface in that the former can be stabilised by methanol, ethanol and acetone. In contrast it cannot be permanently stabilised by a 0.15 M NaCl solution, but only by a much higher concentration of 0.5 M or higher. In addition the "hydrophilic" character of the surfaces is characterised by contact angles of between 20 and 50° whereas "ultrahydrophilic" surfaces have a contact angle of 0-10°. It can be deduced therefrom that previously known "hydrophilic" surfaces must be distinguished from the "ultrahydrophilic" ones. In accordance with the invention ultrahydrophilic surfaces can be stabilised by an exsiccation layer, in which respect it is entirely conceivable that the hydrophilic surfaces can also lead to stabilisation of such a hydrophilic surface, by the method described herein involving exsiccation of solutions with non-volatile constituents.

In accordance with this process for the production of a storable implant with an ultrahydrophilic surface the implant is put into a salt-containing solution which is inert in relation to the ultrahydrophilic surface and which encloses the implant on all sides. In this case it is also possible to use an implant produced in a different fashion, which has similar properties in respect of hydrophilicity with the above-mentioned contact angle hysteresis of less than 10°, preferably less than 5°, upon wetting with water. As mentioned hereinbefore the salt solution can be a solution of a single salt or a combination of various salts in water, in which respect the salt is selected from the group which consists of the groups with an anion from $SO_4^{--}$, $HPO_4^{--}$, $CH_3COO^-$, $Cl^-$, $Br^-$, $NO_4^-$, $ClO_4^-$, $I^-$, $CNS^-$, $ClCH_2COO^-$, $F_3CCOO^-$, $Cl_2CHCOO^-$, $Cl_3CCOO^-$, $Br_3CCOO^-$ or a cation from $NH_4^+$, $Rb^+$, $K^+$, $Na^+$, $Cs^+$, $Li^+$, $Mg^{++}$, $Ca^{++}$, $Ba^{++}$ as well as $(CH_3)_4N^+$, $(C_2H_5)_4N^+$, $(C_3H_7)_4N^+$, $(C_4H_9)_4N^+$.

A development of the process according to the invention then includes the additional step that the implant in a salt-containing aqueous solution which has a total ion concentration of more than 0.5 mol/l, preferably more than 1 mol/l, is introduced into a transport packaging and the transport packaging is closed in gas-tight and liquid-tight fashion.

In accordance with the invention in that way there is also provided a moist packaging which reliably protects the implant with an ultrahydrophilic surface from a reduction in ultrahydrophilia.

Although long-term storage is already made possible in that way, it is preferable for reasons of easier handling that the implant, in a salt-containing solution, without being directly introduced into a packaging, is thus subjected in a careful fashion in relation to temperature, without detrimentally influencing the implant properties, to a process in which the salt-containing solution is evaporated to dryness. For that purpose it is sufficient if the salt solution has a lower concentration than for the wet packaging, as the concentration rises in the course of the "evaporation" operation and exceeds the solubility limit of the salt in the formation of exsiccation layer.

In that case the salt-containing solution is preferably used in an amount and with a salt concentration which after evaporation affords a salt layer covering at least the ultrahydrophilic surface of the implant, with a layer thickness of preferably 1 to 500 µm. Particularly preferably the salt-containing solution, after the evaporation operation, gives a salt layer enclosing the implant on all sides.

The resulting implant thus has the exsiccation layer which is referred to in that way by the inventors and which covers and protects the ultrahydrophilic surface of the implant.

Thus the implant provided with that exsiccation layer can be put into a dry packaging and stored in the long term. Preceding storage sterilisation of the implant is generally performed, sterilisation of the implant preferably including sterilisation with electromagnetic radiation.

Accordingly the invention is also directed to such a storable implant which can be obtained in accordance with the various configurations of the process according to the invention.

BRIEF DESCRIPTION OF THE DRAWINGS

The invention is further described with reference to the accompanying Figures in which:

FIGS. 2A-2C show electron-microscope images of an ultrahydrophilic, nanostructured surface on cp-titanium by the chromosulphuric acid processes at various levels of magnification.

DETAILED DESCRIPTION OF THE INVENTION

Figure 1:
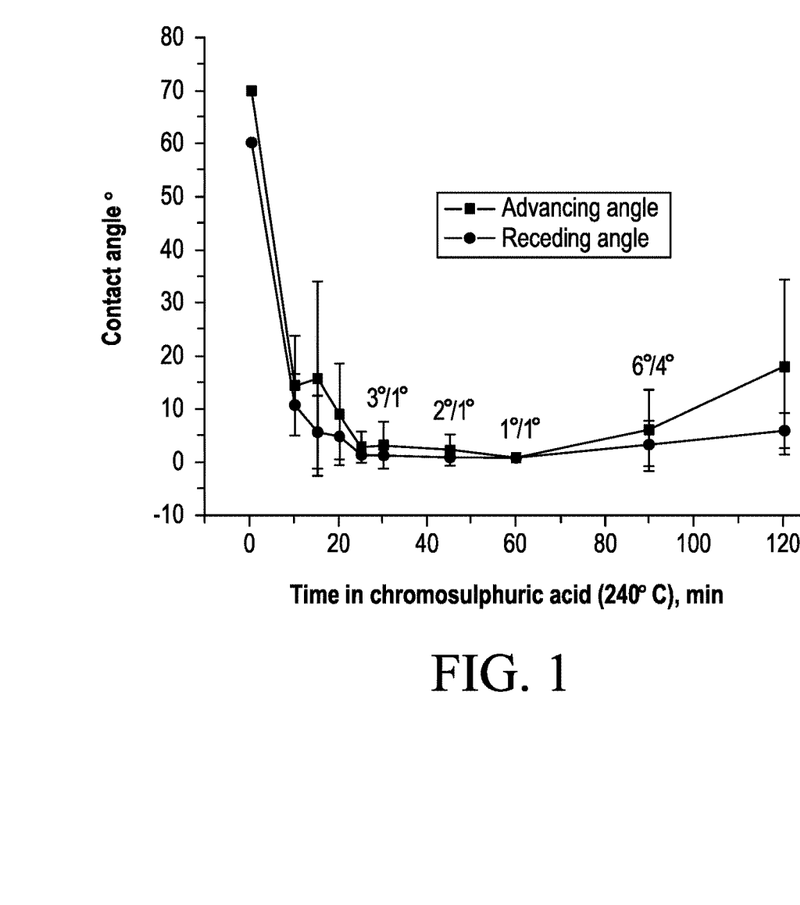
FIG. 1 shows a diagram relating to the magnitude of the advancing and receding angles respectively in relation to the treatment time of a metal surface with chromosulphuric acid.

As FIG. 1 shows treatment of the metal surface with chromosulphuric acid for the production of ultrahydrophilic metal surfaces leads to surprising results. For that purpose titanium plates were incubated at 240° C. in concentrated chromosulphuric acid. As was surprisingly found, ultrahydrophilic surfaces (contact angle: <10°; contact angle hysteresis: ~0°; standard deviations (n=5) are specified), are obtained in a time window of 30-60 minutes.

The inventors found similar minimum curves with 316 L steel, titanium alloys and cobalt-chromium alloys. Table 1 shows that four to five times more BMP-2 can be bonded (adsorbed) on the ultrahydrophilic surface, than on the control. The bonded amount of BMP-2 on the untreated titanium surface is still below the surface treated with $HNO_3$.

Those ultrahydrophilic surfaces have a very high surface energy which in the ultrahydrophilic range (contact angle <11°' contact angle hysteresis~0°) has a critical surface tension $\gamma c=71-72$ dynes/cm. The high surface energy leads to the adsorption of suitable proteins.

Figure 2A:
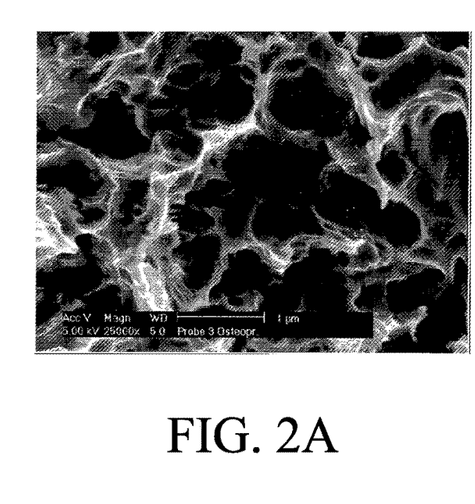
FIG. 2A shows a cleaned Industrial Standard SLA Surface (Sand-Blasted, Large-Grit, Acid-Etched) in a 25,000 Times Magnification.
Figure 2B:
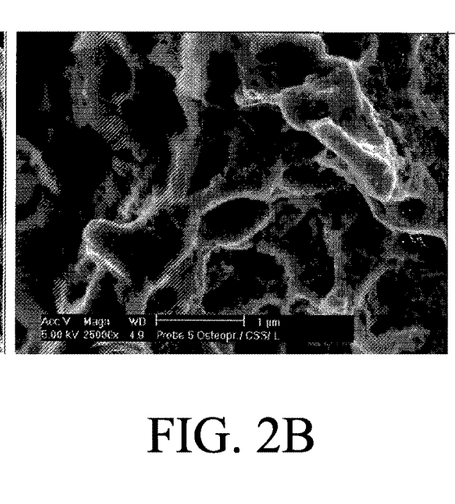
FIG. 2B shows a SLA Surface after Treatment in Chromosulphuric Acid at 240° C. for 60 Minutes in a 25,000 Times Magnification.
Figure 2C:
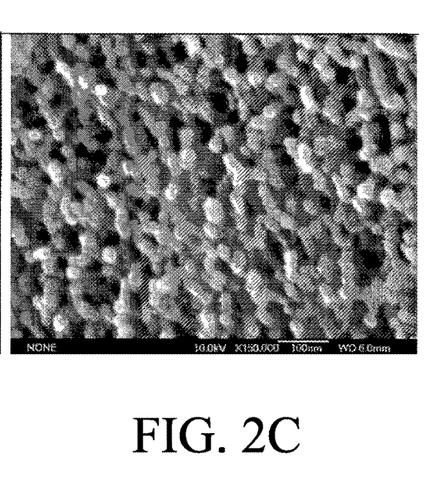
FIG. 2C shows a representation of the Globular Nanostructure at 150,000 Times Magnification on an Electropolished Titanium Surface.

In the production of the ultrahydrophilic surface a novel nanostructure is produced by the new chromosulphuric acid treatment (FIG. 2). Globular, interconnected structures of a diameter of 50-100 nm are produced on the titanium surface which is smooth prior to the treatment, with nanopores of a diameter of 50-100 nm being present between those globular structures. The nanostructures are presumably involved in the provision of ultrahydrophilicity. The conditions in that respect are in detail as follows for illustrations A, B and C:

A. Cleaned Industrial Standard SLA Surface (Sand-Blasted, Large-Grit, Acid-Etched) in a 25,000 Times Magnification The surface was sand-blasted with corundum and then etched in an acid bath ($HCl/H_2SO_4$). The surface exhibits a smooth microstructure without any sign of a nanostructure.

B. SLA Surface after Treatment in Chromosulphuric Acid at 240° C. for 60 Minutes in a 25,000 Times Magnification The chromosulphuric acid functionally produces a hydrophilic surface and structurally a "globular" nanostructure, besides the SLA microstructure. The diameter of the interconnected nano-balls is about 50-100 nm, with nanopores being formed in the same order of magnitude.

C. Representation of the Globular Nanostructure at 150,000 Times Magnification on an Electropolished Titanium Surface The nanospheres are of a diameter of about 50 nm and are connected together. Pores of a diameter of 10-100 nm are formed between the spheres.

In a further step, peptides like bone growth factors can be immobilised on those nanostructures by means of physisorptive or chemisorptive bonding, presumably by virtue of hydrophilic interactions, on the implant material. That makes it possible to produce a chemotactically acting and/or biologically active, so-called juxtacrine implant surface which leads to colonisation, proliferation and differentiation of bone cells. It is thus possible to produce so-called active implants which, in relation to molecules liberated from the surface, exhibit a chemotactic action on cells, in the case of BMPs on osteoblasts, even at a distance of 500 to 1000 μm.

Preferably adequate loading of the oxidised metal surface is achieved by the peptides being applied in a physiological buffer solution in a concentration which is sufficient to achieve a loading of more than 200 $ng/cm^2$, preferably more than 500 $ng/cm^2$ and more preferably more than 1000 $ng/cm^2$ of the peptide on the oxide surface of the metal implant.

In general that loading is achieved with a physiological buffer solution of peptides in a concentration of more than 1 μg/ml, preferably more than 200 μg/ml of buffer solution.

According to the invention the peptides are biomolecules which are advantageous in terms of biocompatibility of the implant insofar as they counteract possible rejection of the implant and/or promote the implant growing into place.

As mentioned hereinbefore preferably proteins from the class of TGF proteins, in particular the bone growth promoting proteins from the class of bone growth factors bone morphogenic proteins, or the class of vessel growth factors such as VEGF or angiotropin or also ubiquitin can be used as peptides. The term transforming growth factor (TGF) is used to denote in particular the group (subgroup) of (i) transforming growth factors beta (TGF-β) and the group (subgroup) of (ii) bone morphogenetic proteins (BMP). The latter are osteoinductive proteins which stimulate bone regeneration and bone healing insofar as they cause proliferation and differentiation of precursor cells to osteoblasts. In addition they promote the formation of alkaline phosphatases, hormone receptors, bone-specific substances such as collagen type 1, osteocalcin, osteopontin, osteonectin, bone sialoprotein (BSP) and finally mineralisation.

Advantageously for immobilisation purposes it is possible to use a protein of that class alone, in combination with further members of that class or also together with biomolecules such as proteins of other classes or low-molecular hormones or also antibiotics to improve immune rejection. In that case those further molecules can also be immobilised on the surface by way of bonds cleavable in the physiological medium.

It was already earlier found on the part of the inventors that the number of oxide groups can surprisingly be increased by the surface of the metal being treated with hot, preferably bottom sediment-free chromosulphuric acid. In contrast to the expectation that the metal dissolves under those conditions, a substantially uniform 5-50 nm thick hydrophilic oxide layer is produced on the surface of the metal when using that acid. The process is so careful that even coronary vessel supports, referred to as stents (which for example can be made from high-quality steel or titanium) can be coated without destroying the thin delicate mesh (50-150 μm diameter). In particular transition metal surfaces cleaned with dilute acid such as titanium, steel, steel alloys such as Cr—Mo-steel or steel or pure titanium surfaces or titanium alloys, treated with chromosulphuric acid, are suitable as materials for the oxide treatment.

Both in the case of polished implants and also in the case of sand-blasted (SLA-surfaces) implants or implants coated with metal plasmas (for example titanium plasma spray or TPS), the ultrahydrophilic oxide layer, after treatment of the metal surface, under defined conditions, can be of a thickness of 10 nm up to 300 nm and can be constructed in the form of nanostructures, as shown in FIG. 2, of different geometries (for example round or polygonal). In that respect pure titanium or titanium alloys (for example (TiAlV4, TiAlFe2,5), aluminium or stainless steel (for example V2A, V4A, chromium-nickel 316 L, Cr-Mo-steel) can be used as metal for the implant. A commercially available chromosulphuric acid with 92% by weight $H_2SO_4$, 1.3% by weight of $CrO_3$ and of a density of 1.8 g/cm$^3$, as is available for example from Merck, is preferably used for producing a thin smooth layer of metal oxide.

The novel process according to the invention allows ultrahydrophilic surfaces to be produced in all cases, in contrast to earlier processes. The three preferred process steps: (i) the novel CSS treatment (shock heating), (ii) quenching in concentrated sulphuric acid, and (iii) the novel EDTA washing method reduce the chromium content (EDX method) on the surface below the detection limit. The EDX detection limit is at 0.2-0.5 atom %. The novel chromium-free ultrahydrophilic surfaces exhibit the particular novel properties set forth hereinafter in respect of BMP-2 bonding and stabilisation by the salt layer.

If a thicker metal oxide layer (>1000 nm) is to be provided at the metal surface and/or preferably an oxide layer with small micro- and nanopores the above-described chromosulphuric acid is diluted with water to a density of 1.5 to 1.6 g/cm$^3$. In a treatment, which then follows as described hereinbefore, of the metal implant surface with the acid diluted in that way, a "rough" surface layer with depressions and pores is formed, so that the surface available for loading with peptides is increased in size. By adjusting different densities in respect of the chromosulphuric acid and different treatment times and temperatures it is therefore possible to apply a multiplicity of different oxide layers with different properties to metal surfaces, with a high level of adhesive strength.

The ultrahydrophilic surface produced by the chromosulphuric acid can impart the hydrophilic properties in respect of prolonged storage in air and in pure water. Under those conditions the contact angle can rise after 1-2 hours to values of 20-40°. The ultrahydrophilic surface can be stabilised in accordance with the invention by means of a salt solution as the stabilisation agent. In accordance with the invention it is also alternatively possible to use as such stabilisation agents, alcohols in the homologous alkane, alkene and alkine series which can be straight-chain or branched and can have up to 20 carbon atoms, in particular up to 6 carbon atoms, in particular water-free methanol and ethanol, as well as phenolic compounds, the latter also in aqueous solution. Preferably, as mentioned hereinbefore, stabilisation is possible by various aqueous salt solutions which can be ordered in accordance with their salting-out effect in relation to proteins (Table 2). These involve for example the anions $SO_4^{--}$, $HPO_4^{--}$, $CH_3COO^-$, $Cl^-$, $Br^-$, $NO_4^-$, $ClO_4^-$, $CNS^-$, $ClCH_2COO^-$, $F_3CCOO^-$, $Cl_2CHCOO^-$, $Cl_3CCOO^-$, $Br_3CCOO^-$ or the cations $NH_4^+$, $Rb^+$, $K^+$, $Na^+$, $Cs^+$, $Li^+$, $Mg^{++}$, $Ca^{++}$, $Ba^{++}$ as well as tetraalkylammonium cations like $(CH_3)_4N^+$, $(C_2H_5)_4N^+$, $(C_3H_7)_4N^+$, $(C_4H_9)_4N^+$. NaCl salt solutions above 0.15 mol/l are preferred, particularly preferred above 0.5 mol/l, quite particularly preferred in the region of 1 mol/l. The ultrahydrophilic surfaces are almost unlimitedly stable in such solutions. Such high levels of salt concentration occur for short times during evaporation even from dilute buffer mixtures as specified hereinbefore. A preferred salt concentration in the buffer solution is 135 to 140 mM NaCl, 8 to 8.2 mM $Na_2HPO_4$, 2.6 to 2.8 mM KCl, 1.4 to 1.6 mM $KH_2PO_4$ at a pH in the range of 7.3 to 7.5. Evaporation to dryness leads to high local levels of salt concentration. In that respect the $HPO_4^{--}$, which has substantially stronger salting-out properties than $Cl^-$ can exert a particular stabilising influence on the oxide layer.

The invention is therefore also directed to a process of making the implants provided with an oxide layer with nanostructures storage-stable by means of such "stabilisation agents".

In the most general form the present invention therefore also concerns a process for stabilisation of the ultrahydrophilic surfaces by shielding the surfaces from influences which detrimentally influence ultrahydrophilicity. Thus an embodiment of the process according to the invention is also directed to the implant with a hydrophilic surface being put into a solvent which contains dissolved therein a coating agent which detrimentally influences the ultrahydrophilic surface neither in solution nor in the coating. The solvent is evaporated and the coating agent remains behind on the implant with the ultrahydrophilic surface and encloses the implant. In that way the implant can reliably preserved for long-term storage. An embodiment of the solution with coating agent can be the above-described aqueous salt solution which easily acquires salting-out properties upon evaporation. A further embodiment can be a solution of a zwitterionic organic substance, for example an amino acid, for example glycine, which can have a similar salting-out effect as $SO_4^{--}$, $HPO_4^{--}$. Further non-volatile organic substances can be polyhydric alcohols like glycerine or monosaccharides like glucose and also disaccharides like sucrose as well as inositols which also have a strong influence on the water structure of a surface and which afford a coating after evaporation of the solvent.

The implants coated in accordance with the invention have long-term storage stability and can be used after washing off the coating of salts or organic coating agent for loading with the peptides acting as mediators.

The invention is thus also directed to a process for loading the surface of an implant with peptides, in which peptides are applied to the surface of the implant, which are immobilised on the surface of the implant as a result of physisorptive or chemisorptive interactions between the peptides and the ultrahydrophilic surface of the implant.

In that respect the peptides are used in a physiological buffer solution at a concentration which is sufficient to achieve a loading of more than 200 ng/cm$^2$, preferably more than 500 ng/cm$^2$ and more preferably more than 1,000 ng/cm$^2$ of the peptide on the oxide surface of the metal implant.

In general the peptides are used in a physiological buffer solution in a concentration of more than 1 µg/ml, preferably more than 200 µg/ml of buffer solution.

In accordance with the invention growth factors from the class of TGF proteins, in particular the BMP proteins, preferably BMP-2 or BMP-7, the vessel growth factors such as VEGF or angiotropin, ubiquitin, antibiotics or mixtures thereof are used as peptides.

If the mediators used are difficult to dissolve in the medium under the coupling conditions, solubility can be increased by the addition of surfactants and/or detergents and the reaction can be performed. Thus, bone growth factors and other mediators which are difficult to dissolve, at pH-values >6, can be kept in solution by ionic or non-ionic detergents in the concentration range of 0.05-10%, preferably 1-5% by weight, in particular at 0.066% SDS at pH-values >6, in particular at pH 8-12, quite particularly pH 9-11, especially pH 10.0, for bonding processes in the alkaline pH range without a loss in biological activity. Thus the invention is also directed to a process for the production of implants coated with peptides, in which the implant with an ultrahydrophilic surface is treated with a preferably alkaline buffer solution containing one or more detergents. Such a process can include in particular a treatment with an NBS buffer comprising 125 mM Na-borate buffer, 0.066% sodium dodecylsulphate (pH 10.0).

Accordingly the invention is also directed to a process of loading implants with bone growth factors, in particular BMP-2, in which the ultrahydrophilic surface of the implant is treated with a solution of the bone growth factor at a pH-value of 9 to 11, preferably 10. For that purpose for example an implant, for example the implant removed from the dry packaging and still covered with the exsiccation layer, is preferably directly treated with a buffered solution of the bone growth factor at a pH-value of 9 to 11, preferably 10, without the exsiccation layer having to be previously washed off.

Surprisingly therefore the inventors succeeded in producing a coating on the ultrahydrophilic surface of an implant which is selected from metallic materials such as pure titanium, metallic titanium alloys, chromium/nickel/aluminium/vanadium/cobalt alloys (for example TiAlV4, TiAlFe2,5), high-quality steels (for example V2A, V4A, chromium-nickel 316 L), ceramic materials, in particular hydroxyapatite, aluminium oxide or a combination of the metallic materials with ceramic materials thereof, in which the metallic material is in the form of a composite material with ceramic material, with bone growth factors, in particular BMP-2, wherein the coating on the ultrahydrophilic surface is performed in aqueous buffered solution either in the acid range in the range between pH 4 and 5, in particular at pH 4.5, or in the weakly alkaline range between pH 9 and 11, preferably pH 10. The coating operation in the alkaline range can advantageously be effected in the presence of detergents such as SDS.

A particularly preferred embodiment of the process according to the invention provides for applying to the ultrahydrophilic surface of the implant BMP-2 or BMP-7 in a physiological buffer solution in a concentration of more than 1 µg BMP-2 or BMP-7/ml buffer solution, preferably more than 200 µg BMP-2 or BMP-7/ml buffer solution. Those aforementioned concentrations are generally sufficient to achieve a loading of more than 200 ng BMP-2 or BMP-7/cm$^2$, preferably more than 500 ng BMP-2 or BMP-7/cm$^2$ and more preferably more than 1000 ng BMP-2 or BMP-7/cm$^2$ of the peptide on the oxidised surface of the metal implant.

The implants with an ultrahydrophilic surface, produced by means of the process according to the invention, are also subject-matter of the invention. Thus the invention also concerns implants in which the implant material comprises titanium, titanium alloys, aluminium, stainless steel, steel alloys, chromium-bearing alloys, ceramic materials such as hydroxyapatite or combinations thereof. In that case the implant can be a joint or bone prosthesis, a dental implant or in particular a coronary vessel support coated with a peptide, for example BMP-2 (a so-called coronary stent, length about 10 mm) to therapeutically prevent or alleviate the later complication of restenosis caused by proliferation of smooth vessel muscle cells, in order thereby to promote healing and compatibility.

The influence of the materials modified in accordance with the process of the invention on bone cells was investigated in animal experiments, the modified materials being produced for that purpose in plate or dumbbell form. It was observed in that case that, 4 weeks after being introduced into the animals, accelerated bone formation occurred with contact in relation to the implant surface by BMP-2 on the materials.

The present invention is set forth in further detail by reference to the following examples.

Modification of Metals (Titanium, 316 L Stainless Steel):

The experiments described hereinafter involved the use of either mechanically polished/electropolished, anodically oxidised titanium plates, titanium alloy plates pre-etched with other acids, sand-blasted or plasma-sprayed with porous titanium alloy, with or without chromosulphuric acid treatment. Equally stainless, mechanically polished/electropolished steels are used, with or without chromosulphuric acid treatment.

Cleaning Process

Prior to each use the materials were cleaned by heating at 80° C. in 5% HNO$_3$ for 2 hours. After renewed washing in water the plates were dried by washing in 30 ml in dry methanol. Thereafter they were either directly further used or treated with chromosulphuric acid.

Chromosulphuric Acid Treatment

In the chromosulphuric acid treatment the titanium plates were shock-heated at 210-240° C. in chromosulphuric acid (92% $H_2SO_4$, 1.35 $CrO_3$), incubated for 30-90 min at that temperature and then quenched with concentrated sulphuric acid at room temperature. Thereupon the metal samples were washed with 10×50 ml water, treated with 2×30 min 10% EDTA ((pH 7) ultrasound) and then 1-3×30 min in boiling 10% EDTA (pH 7) and thereafter washed for 30 min with boiling water and rinsed with water. That resulted in an ultrahydrophilic surface which is substantially chromate-free, that is to say no free chromium ions can now be detected on the surface.

EXAMPLE 1

Immobilisation of rhBMP-2 on Ultrahydrophilic Titanium Plates

The pretreated titanium plates were washed with 125 mM Na-borate buffer, 0.066% sodium dodecylsulphate, pH 10.0, and equilibriumed. BMP-2 which was initially present in 50 mM tris, pH 8.0, 1000 mM NaCl, 5 mM EDTA, 33 mM 3-[(3-cholamido-propyl)dimethylammonio]-propane sulfonic acid buffer (=CPDP buffer) was dialysed in relation to 125 mM Na-borate buffer, 0.066% sodium dodecylsulphate, pH 10.0 (=NBS buffer) and incubated in a concentration of 0.2-0.3 mg/ml for 12-14 hours at room temperature with shaking with the titanium plates. Thereupon they were washed 4× with borate buffer and then with water.

TABLE 1 immobilisation of rhBMP-2 on HNO3-treated or chromosulphuric acid-treated titanium plates (5 × 10 × 1 mm)

| Modification of electropolished titanium | Immobilised 125I-rhBMP-2 [ng/cm2] |
|---|---|
| HNO3-treated ($\theta_A/\theta_R = 40°/20°$) | 273 ± 107 (4) |
| ultrahydrophilic ($\theta_A/\theta_R = 1°/1°$) | 1272 ± 636 (4) |

Immobilisation buffer: 125 mM borate/0.066% SDS, pH 10.0, $C_{rhBMP-2}$ = 0.25 mg/ml, n = 4.
$\theta_A$: dynamic advancing angle,
$\theta_R$: dynamic receding angle

TABLE 2 ordering of the salts according to their salting-out and salting-in effect in relation to proteins

| Salting-out effect | Salting-in effect |
|---|---|

Anionic:

$SO_4^- > HPO_4^{--} > CH_3COO^- > Cl^- > Br^- > NO_4^- > ClO_4^- > I^- > CNS^-$
$CH_3COO^- > ClCH_2COO^- > F_3CCOO^- > Cl_2CHCOO^- >$
$Cl_3CCOO^- > Br_3CCOO^-$

Cationic:

$(CH_3)_4N^+ > NH_4^+ > Rb^+, K^+, Na^+, Cs^+ > Li^+ > Mg^{++} > Ca^{++} > Ba^{++}$

Cationic/hydrophobic $(CH_3)_4N^+ > (C_2H_5)_4N^+ >> (C_3H_7)_4N^+, (C_4H_9)_4N^+$ The action of the salts occurs inter alia by way of the water structure. The salts stabilise or destabilise the ultra-hydrophilic surface by way of the water molecules bonded to the surface and ionic groups. NaCl salt solutions involving 0.15 mol/l are preferred, particularly preferably 0.5 mol/l, quite particularly preferably in the region of 1 mol/l.

EXAMPLE 2

Liberation of rhBMP-2 from Ultrahydrophilic Titanium Plates

Figure 3:
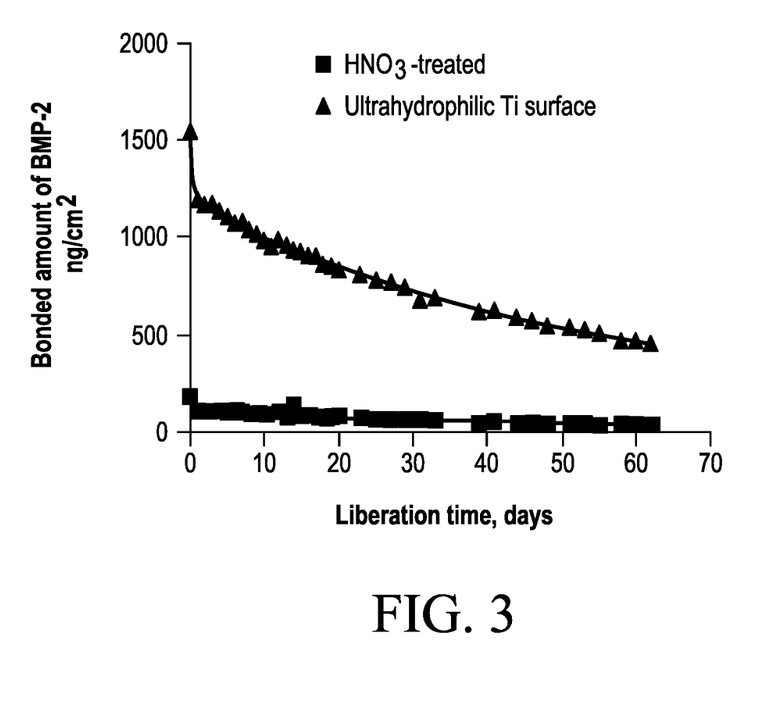
FIG. 3 shows a diagram relating to the liberation rate of BMP of metal surfaces subjected to various treatments.

As shown in FIG. 3 the adsorption of rhBMP-2 on an ultrahydrophilic titanium surface and liberation from the surface is markedly improved in comparison with a titanium surface only treated with dilute HNO3 for cleaning purposes, as can be seen by reference to the liberation kinetics, shown in FIG. 3, of rhBMP-2 from an ultrahydrophilic titanium surface. The great capacity differences will also be clear. The illustrated liberation curves can be adapted with a 3-phase exponential function. In the case of the control there are actually only 2 phases. Liberation has been measured over 62 days. The half-value times of liberation and the amounts of rhBMP-2 liberated are set out in Table 3.

TABLE 3

Liberation of rhBMP-2 from Ultrahydrophilic Titanium Plates

| | HNO3-treatment ($\theta_A/\theta_R = 40°/20°$) $\Gamma_0$ = 181 ng/cm$^2$ | | Ultrahydrophilic titanium surface ($\theta_A/\theta_R = 1°/1°$) $\Gamma_0$ = 1551 ng/cm$^2$ | |
|---|---|---|---|---|
| Liberation phase | T½ days | Liberated amount/day ng/day | T½ days | Liberated amount/day ng/day |
| 1st phase (2 days) | 0.28 | 36 | 0.37 | 193 |
| 2nd phase (42 days) | 39 | 0.5 | 33 | 14 |
| 3rd phase (18 days) | 39 | 0.5 | 231 | 7 |
| Total amount liberated in 62 days: | | 102 | | 1100 |

$\Gamma_0$: Immobilised rhBMP-2 amount/cm$^2$ at the time t = 0.

Figure 5A:
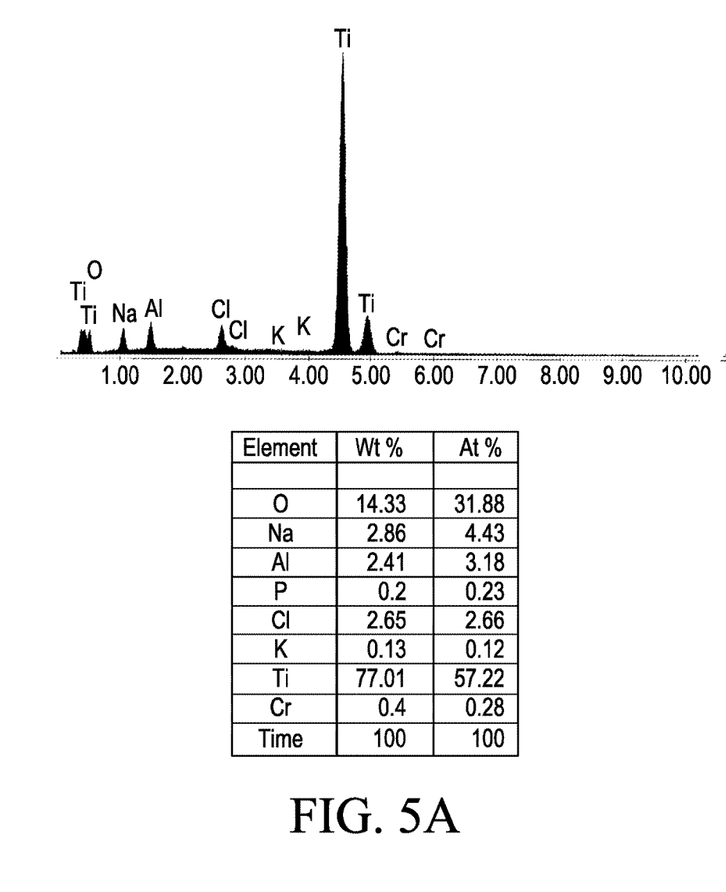
FIGS. 5A-5B show the EDX analysis of an ultrahydrophilic plate with exsiccation layer after gamma sterilisation (FIG. 5A) and after removal of the exsiccation layer with water (FIG. 5B).
Figure 5B:
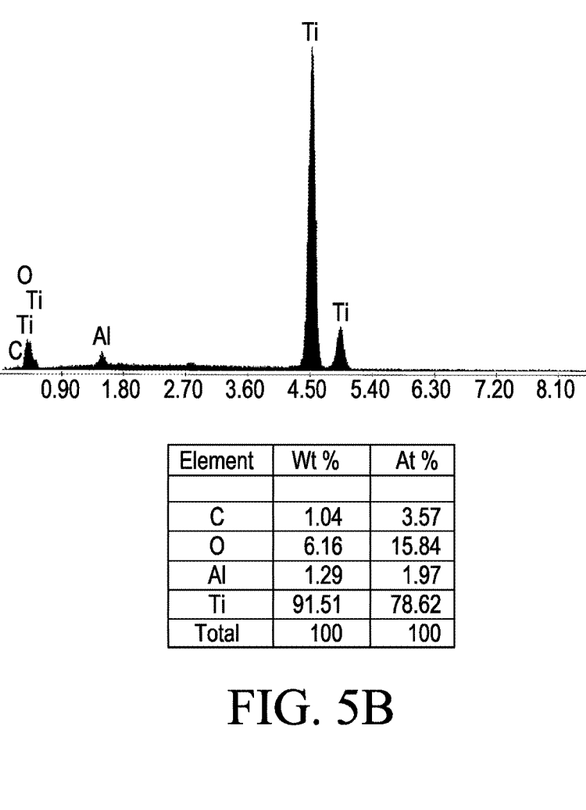

As can be seen from FIG. 4 the scanning electron-microscope recordings of chromosulphuric acid-treated SLA titanium plates (14×14×1.5 mm) after gamma sterilisation in an exsiccation buffer (60 min CSS with HNO$_3$, with quenching, gamma sterilised in PBS, $\theta$=0°) show a sterilised ultrahydrophilic titanium oxide surface, provided with microcaverns, with a protective layer of dried-in exsiccation buffer which after washing off of the "exsiccation protective layer" gives a purely ultrahydrophilic titanium oxide surface as, as shown in FIG. 5, the EDX analyses of an ultrahydrophilic plate with exsiccation layer after gamma sterilisation (A) and after removal of the exsiccation layer with water (B) show.

The storage stability of the ultrahydrophilic surfaces is shown by means of the dependency of the dynamic contact angles of gamma-sterilised, ultrahydrophilic SLA titanium plates (14×14×1.5 mm) provided with an exsiccation layer according to the invention, on the storage time as set forth in Table 4, wherein the reference to SLA titanium plates is used to denote titanium plates which have sand-blasted and acid-etched surfaces. As shown, an "unprotected" hydrophilic surface is already less hydrophilic after a few hours in air while the contact angles of the gamma-sterilised, ultra-hydrophilic SLA titanium plates provided with the exsiccation layer according to the invention are almost constant without change at 0° after up to 24 weeks storage.

TABLE 4

| | Sample prior to chromosulphuric acid treatment | | Storage time after chromosulphuric acid treatment (exsiccation-coated and gamma-sterilised) | | | | | | | | | | | | | |
|---|---|---|---|---|---|---|---|---|---|---|---|---|---|---|---|---|
| | 18 hours stored in air | | control (0-days) | | 6 days | | 15 days | | 4 weeks | | 8 weeks | | 18 weeks | | 24 weeks | |
| | Dynamic contact angles according to Wilhelmy | | | | | | | | | | | | | | | |
| Sample | $\theta_A$ | $\theta_R$ | $\theta_A$ | $\theta_R$ | $\theta_A$ | $\theta_R$ | $\theta_A$ | $\theta_R$ | $\theta_A$ | $\theta_R$ | $\theta_A$ | $\theta_R$ | $\theta_A$ | $\theta_R$ | $\theta_A$ | $\theta_R$ |
| SLA-1 | 59.2 | 0.0 | 0.0 | 0.0 | 0.0 | 0.0 | 6.1 | 0.0 | 0.0 | 0.0 | 0.0 | 0.0 | 0.0 | 0.0 | 0.0 | 0.0 |
| SLA-2 | 53.3 | 0.0 | 0.0 | 0.0 | 5.7 | 0.0 | 0.0 | 0.0 | 0.0 | 0.0 | 0.0 | 0.0 | 0.0 | 0.0 | 0.0 | 0.0 |
| SLA-3 | 100.8 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| SLA-4 | 94.3 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| SLA-5 | 86.5 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Average value(L) | 78.8 | 0.0 | 0.0 | 0.0 | 1.1 | 0.0 | 1.2 | 0.0 | 0.0 | 0.0 | 0.0 | 0.0 | 0.0 | 0.0 | 0.0 | 0.0 |
| Standard deviation (s) | 21.3 | 0.0 | 0.0 | 0.0 | 2.5 | 0.0 | 2.7 | 0.0 | 0.0 | 0.0 | 0.0 | 0.0 | 0.0 | 0.0 | 0.0 | 0.0 |

The invention claimed is:

1. A storable implant, comprising:
an implant material having an ultrahydrophilic surface, wherein said implant material is selected from the group consisting of- pure titanium, metallic titanium alloys, chromium/nickel/aluminum/vanadium/cobalt alloys, TiAlV4, TiAlFe$_{2.5}$, steels, V2A, V4A, chromium-nickel 316L, ceramic materials, hydroxyapatite, aluminum oxide, and combinations thereof with ceramic materials,
wherein said ultrahydrophilic surface comprises an oxide layer, and
wherein said ultrahydrophilic surface further comprises a salt layer.

2. The storable implant of claim 1, wherein the salt layer covers at least the ultrahydrophilic surface and has a layer thickness of 1 to 500 μm.

3. The storable implant of claim 1, wherein the salt layer encloses the ultrahydrophilic surface on all sides.

4. The storable implant of claim 1, wherein the ultrahydrophilic surface is sterile.

5. A packaged storable implant, comprising:
an implant material having an ultrahydrophilic surface, wherein said implant material is selected from the group consisting of- pure titanium, metallic titanium alloys, chromium/nickel/aluminum/vanadium/cobalt alloys, TiAlV4, TiAlFe$_{2.5}$, steels, V2A, V4A, chromium-nickel 316L, ceramic materials, hydroxyapatite, aluminum oxide, and combinations thereof with ceramic materials,
wherein said ultrahydrophilic surface comprises an oxide layer, and
wherein said ultrahydrophilic surface further comprises a salt layer, wherein said ultrahydrophilic surfaces comprises an oxide layer, wherein the implant material is in a transport packaging, wherein said transport packaging is closed in gas-tight and liquid-tight fashion, wherein said transport packaging further comprises a salt-containing aqueous solution which is inert in relation to the ultrahydrophilic surface and which encloses the implant material on all sides, wherein said salt-containing aqueous solution has a total ion concentration of more than 0.5mol/L.

6. The packaged storable implant of claim 5, wherein the salt-containing aqueous solution has a total ion concentration of more than 1 mol/L.

7. The packaged storable implant of claim 5, wherein the ultrahydrophilic surface is sterile.

* * * * *